(12) United States Patent
Luber et al.

(10) Patent No.: US 11,747,464 B2
(45) Date of Patent: Sep. 5, 2023

(54) AGRICULTURAL DETECTION DEVICE AND A DETECTION METHOD FOR SENSING AGRICULTURAL OBJECTS

(71) Applicant: Pepperl+Fuchs SE, Mannheim (DE)

(72) Inventors: Ernst Luber, Neukirchen (DE); Philipp Seitz, Hirschbach (DE)

(73) Assignee: Pepperl + Fuchs SE, Mannheim (DE)

( * ) Notice: Subject to any disclaimer, the term of this patent is extended or adjusted under 35 U.S.C. 154(b) by 314 days.

(21) Appl. No.: 16/531,723

(22) Filed: Aug. 5, 2019

(65) Prior Publication Data

US 2020/0041639 A1 Feb. 6, 2020

(30) Foreign Application Priority Data

Aug. 3, 2018 (DE) ............... 10 2018 006 128.1

(51) Int. Cl.
*G01S 13/86* (2006.01)
*G01N 33/02* (2006.01)
*A01M 7/00* (2006.01)

(52) U.S. Cl.
CPC .......... *G01S 13/862* (2013.01); *G01N 33/025* (2013.01); *A01M 7/0089* (2013.01)

(58) Field of Classification Search
CPC ........ G01S 13/862; G01S 15/87; G01S 15/88; G01S 15/8934; A01M 7/0057
See application file for complete search history.

(56) References Cited

U.S. PATENT DOCUMENTS

| | | | |
|---|---|---|---|
| 5,712,640 A | 1/1998 | Andou et al. | |
| 8,031,556 B2 | 10/2011 | Magane et al. | |
| 8,843,283 B2 | 9/2014 | Strelioff et al. | |
| 9,383,443 B2 | 7/2016 | Bartyila | |
| 10,033,098 B2 | 7/2018 | Schoor | |
| 2009/0009306 A1* | 1/2009 | Magane | G01S 15/931 340/435 |

(Continued)

FOREIGN PATENT DOCUMENTS

| CN | 101339249 A | 1/2009 |
|---|---|---|
| CN | 104541180 A | 4/2015 |

(Continued)

OTHER PUBLICATIONS

Chinese Search Report in corresponding application 201910710445.1.

*Primary Examiner* — Timothy A Brainard
*Assistant Examiner* — Juliana Cross
(74) *Attorney, Agent, or Firm* — Muncy, Geissler, Olds & Lowe , P.C.

(57) ABSTRACT

Agricultural detection device, having a sensor unit, an evaluation unit and a control unit. The sensor unit includes a first sensor with a first directivity and is configured to emit a first transmission signal and to receive a first reflection signal. The first sensor has a second directivity and emits a second sensor signal with the second directivity and receives a second reflection signal, or the sensor unit has a second sensor with a second directivity arranged adjacent to the first sensor for emitting the second transmission signal and for receiving the second reflection signal. The evaluation unit is configured to ascertain at least the structure of plants and a height value from the first reflection signal and the second reflection signal.

14 Claims, 2 Drawing Sheets

(56) References Cited

U.S. PATENT DOCUMENTS

| | | | | |
|---|---|---|---|---|
| 2013/0345937 | A1* | 12/2013 | Strelioff | A01D 41/141 |
| | | | | 701/50 |
| 2015/0015697 | A1* | 1/2015 | Redden | A01G 7/00 |
| | | | | 382/110 |
| 2020/0196527 | A1* | 6/2020 | Ferrari | A01B 69/001 |

FOREIGN PATENT DOCUMENTS

| | | | | |
|---|---|---|---|---|
| CN | 105074497 | A | 11/2015 | |
| DE | 102011017621 | A1 | 10/2012 | |
| DE | 102015111264 | A1 | 1/2017 | |
| EP | 1978433 | A2 | 10/2008 | |
| EP | 2630856 | A2 | 8/2013 | |
| EP | 2679685 | A1 | 1/2014 | |
| FR | 3019969 | A1 | 10/2015 | |
| JP | 3302849 | B2 | 7/2002 | |
| WO | WO-2019169434 | A1 * | 9/2019 | G01J 3/0208 |

* cited by examiner

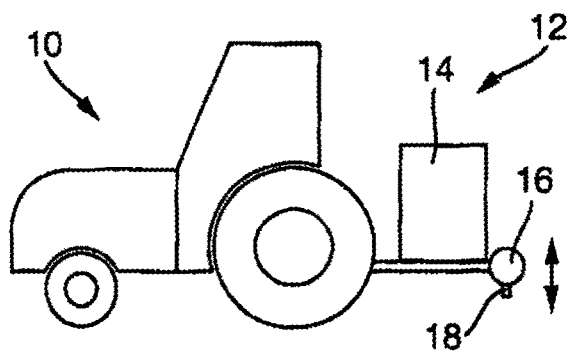
Fig. 1
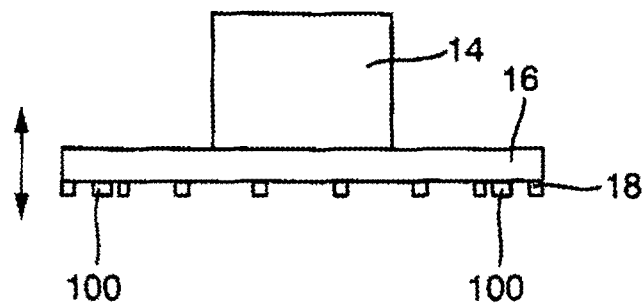
Fig. 2
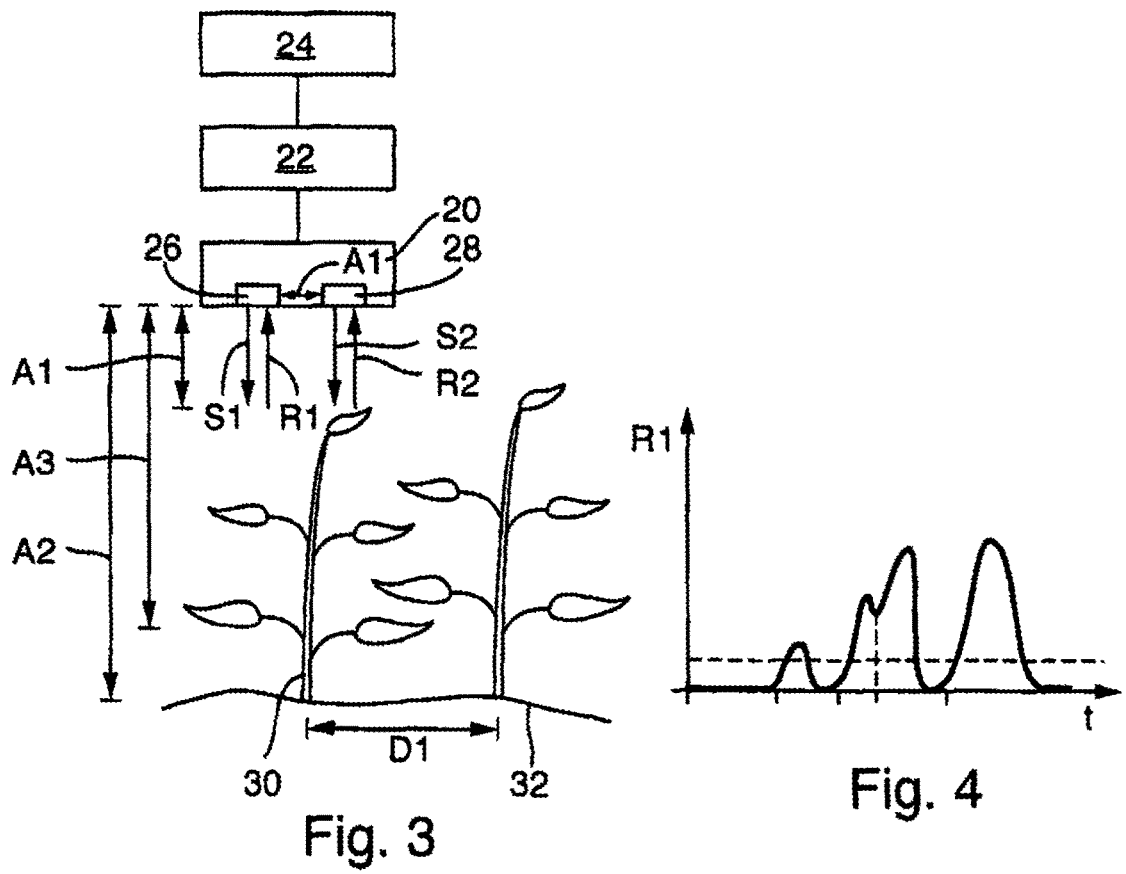
Fig. 3
Fig. 4

AGRICULTURAL DETECTION DEVICE AND A DETECTION METHOD FOR SENSING AGRICULTURAL OBJECTS

This nonprovisional application claims priority under 35 U.S.C. § 119(a) to German Patent Application No. 10 2018 006 128.1, which was filed in Germany on Aug. 3, 2018, and which is herein incorporated by reference.

BACKGROUND OF THE INVENTION

Field of the Invention

The present invention relates to an agricultural detection device and a detection method for sensing agricultural objects.

Description of the Background Art

From EP 2 679 085 A1, which corresponds to U.S. Pat. No. 8,843,283, a method is known for detecting the spray nozzle of a field sprayer to the plants to be sprayed, in which measuring errors or missing readings are compensated in that an average plant height is ascertained using existing readings and a virtual measured value or a substitute value is calculated by means of the average plant height.

SUMMARY OF THE INVENTION

It is therefore an object of the present invention to provide a device which further develops the state of the art.

According to an exemplary embodiment of the invention, provided is an agricultural detection device for detecting agricultural objects, comprising a sensor unit, an evaluation unit and a control unit.

The sensor unit includes a first sensor with a first directivity.

The first sensor is configured to emit a first transmission signal and to receive a first reflection signal.

The first sensor can have a second directivity and can emit a second sensor signal with the second directivity and receives a second reflection signal.

For sending the second transmission signal and for receiving the second reflection signal, the sensor unit can comprise, for example, a second sensor, which is arranged adjacent to the first sensor, with a second directivity.

The first directivity should be smaller in width than the second directivity.

The control unit can be configured to switch between the first directivity and the second directivity.

The evaluation unit can be configured to ascertain the structure of plants and the height of plants from the first reflection signal and the second reflection signal.

The invention further relates to detection methods for the detection of agricultural objects, wherein a sensor unit having a first sensor and an evaluation unit, and a control unit are provided.

The first sensor is in operative connection with the evaluation unit and the control unit.

By means of the first sensor with a first directivity, in each case a first transmission signal is sent at timed intervals and in each case subsequently, a first reflection signal is received.

By means of the first sensor with a second directivity or by means of a second sensor with a second directivity, which is disposed adjacent to the first sensor, in each case a second transmission signal is sent at timed intervals and in each case subsequently, a second reflection signal is received.

The first directivity should be smaller in width than the second directivity.

By means of the evaluation unit, a height value and the structure of a plant are ascertained from the first reflection signal and the second reflection signal.

By means of the control unit, switching between the first directivity and the second directivity takes place. It is understood that preferably, the switchover between the first directivity and the second directivity alternates.

An advantage is that by switching the directivity, the structure of the plants and the distance between the plants can be quickly and reliably ascertained. In particular when applying active substances on the plants, it is beneficial to be able to measure out the amount of the substance during spraying.

The agricultural detection device can be arranged on agricultural tools, for example, on a sprayer.

A field sprayer is an agricultural tool which is able to uniformly spread pesticides or liquid fertilizer on agricultural land.

In field sprayers, the spray mixture is pressurized by a liquid pump located downstream of the tank and then dispensed via spray nozzles. The spray nozzles are typically arranged along a boom, transverse to the direction of movement.

The detection device according to the invention or the respective detection method are designed to ascertain at least a height value. The height value includes in particular the distance of the sensor unit to the ground or to a plant or parts of a plant.

For this purpose, the detection device according to the invention or at least the sensor unit of the detection device can be, for example, disposed on the boom of the field sprayer adjacent to the nozzles so that it is moved along with the sprayer and is at the same distance to the plants or the ground.

The distance control device can ascertain the distance to an object, e.g., the surface to be treated or a structured surface, namely the plants in a field, by means of the duration of a signal transmitted and reflected on the object or the surface of the object.

Thus, the time between emitting a signal, e.g., an ultrasonic pulse, and the subsequent receipt of the transmission signal reflected on surfaces, which here is called a reflection signal, is measured.

In particular, distances are detected by means of two different directivities. The directivity of a sensor describes the angular dependence of the strength of the received or transmitted signals.

In the case of sound sensors, e.g., ultrasonic transducers, one typically speaks of a sound beam. For radar sensors, usually one speaks of a detection field.

Accordingly, different directivities can be realized by sensors or also by different sensor types that are similar but configured or operated differently, i.e., sensors with different physical active principles.

The combination of a narrow and a broad directivity makes it possible to reliably ascertain the distance even at low plant density. In addition, the combination also makes detecting horizontal distances between the individual plants possible, as well as simultaneous reliable detection of the plant tip on the one hand and of the ground on the other.

Thus, additionally the height of the plants as well as the density of the plants can be ascertained and from this, the plant mass is obtained. As a result, in particular the amount of fertilizer applied can be adjusted to the real need of the plants and the expected harvest can be estimated and costs can be saved. Furthermore, the impact on the environment is reduced.

The combination of the measurement results can be based on the fact that these are captured as much as possible at or from the same place, which is why the first and second sensor unit are arranged adjacent to one another. Preferably, the distance between the sensors should be as small as possible.

The distance from the center of the transmission signal source of the first sensor to the center of the transmission signal source of the second sensor preferably should amount to at most 10 cm or at most 5 cm or at most 1 cm.

The first sensor can be an ultrasonic sensor. The first directivity can be a sound beam, e.g., of an ultrasonic transducer, wherein the sound beam can have a width between 30 cm and 70 cm at a distance of 1 cm to the first sensor.

The second directivity can be a sound beam and the sound beam can have a width between 80 cm and 120 cm at a distance of 1 m to the first sensor.

The second sound beam can be a second sensor or, alternatively, the first sensor, wherein for this purpose the first sensor is formed, for example, as an ultrasound transducer with variable directivity.

The second sensor can be a radar sensor with a detection field as the second directivity, wherein the detection field can have a width between 80 cm and 2 m at a distance of 1 m to the radar sensor.

The second transmission signal can be transmitted by means of a second sensor, wherein in each case a first and a second transmission signal are transmitted simultaneously or at least substantially simultaneously.

The first transmission signals and the second transmission signals can be transmitted in alternation. The second transmission signals can be generated and received by the first sensor with a correspondingly variable directivity, or by a second sensor.

The first transmission signals can be generated by means of a first ultrasonic transducer.

The second transmission signals can be generated by means of a second ultrasonic transducer or by means of a radar sensor.

A rising slope can be ascertained in the reflection signals by means of a slope threshold.

A height value can be ascertained in the reflection signals by means of a height threshold. The threshold comparisons can be performed by means of digital threshold filters.

A reflection of the transmission signal on a surface causes a peak, i.e., various reflections from different reflection planes of the plant to the ground cause different or a plurality of peaks in the reflection signal.

The individual peaks can be recognized either on the basis of the rise, i.e. the rising slope or an increase in the slope of the signal, or on the basis of the especially high signal values in the area of the peak tip.

A height value can be ascertained after passing a slope threshold and a height threshold. By means of a slope threshold, the beginning of a rising slope is ascertained.

If a slope threshold is subsequently undershot, this signifies the end of the slope. If the height of the slope additionally exceeds a height threshold, the slope is considered a reflection. For example, the time point of the slope rise, that is, the point in time when the slope threshold is exceeded, is considered the beginning of the reflection.

The combination of the two threshold filters provides a particularly reliable evaluation of the reflection signals. In particular, individual reflection planes of a plant can be detected more accurately.

The height values can be ascertained by means of a dynamic thresholding method.

For example, to carry out one or more thresholding queries, the evaluation unit can include appropriate digital filters in the form of logic building blocks or in the form of a signal processor with a program.

The evaluation unit can be configured to regulate the height of the agricultural tool from the height value. In this case, the height value of the agricultural tool includes the distance of the boom or the spray nozzles to a surface to be treated, e.g., the soil and/or plants, i.e. plant tips. A uniform distance between the spray nozzles and the plants to be treated allows for reliable, resource-saving treatment.

By means of the height value, it is possible during operation to adapt, i.e. regulate in particular the distance of the nozzles as quickly as possible to a change in the plant height.

Further scope of applicability of the present invention will become apparent from the detailed description given hereinafter. However, it should be understood that the detailed description and specific examples, while indicating preferred embodiments of the invention, are given by way of illustration only, since various changes, combinations, and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein:

FIG. 1 is a side view of a first arrangement according to the invention of an inventive detection device on a field sprayer, FIG. 2 is a rear view of the field sprayer from FIG. 1, FIG. 3 is a view of a detection device, FIG. 4 is a view of a first reflection signal.

DETAILED DESCRIPTION

Figure 5:
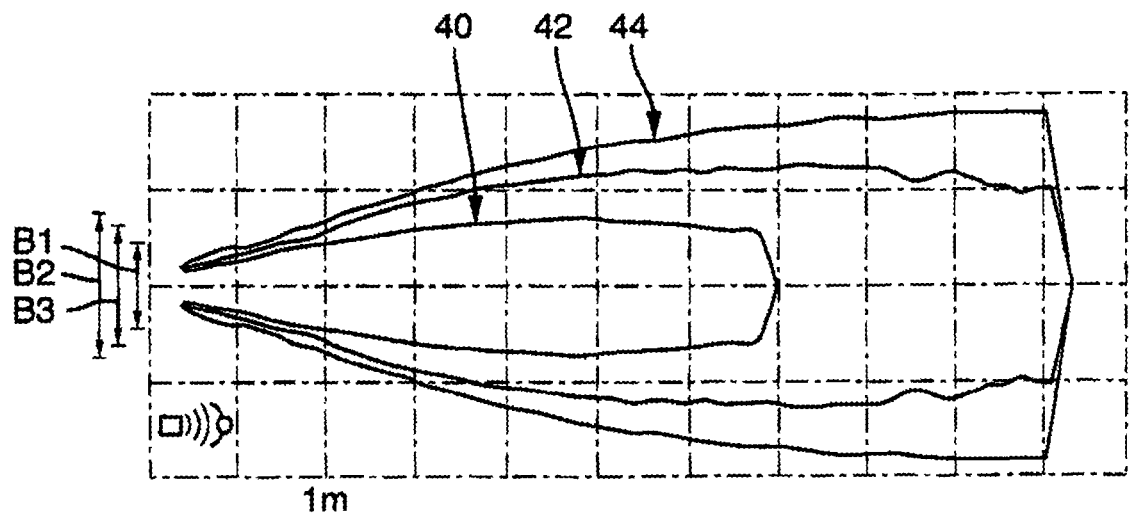
FIG. 5 is a view of sound beams of an ultrasonic sensor for different transmitting powers and FIG. 6 is a view of sound beams of various ultrasonic sensors.

The illustrations of FIG. 1 and FIG. 2 show a tractor 10 comprising a field sprayer 12 in a side view or a rear view. The field sprayer 12 includes a tank 14 for the spray mixture as well as a spray boom 16. Spray nozzles 18 are arranged along the spray boom 16.

The spray boom 16 of the field sprayer 12 is fixed in height, or can be moveable in a vertical direction.

In order to ascertain the distance of the spray nozzles 18 to the ground and/or the plants or varying plant layers, such as the size of the plants and the density of the plant growth, at least a part of the inventive detection device 100 is arranged on the spray boom 16 adjacent to at least one spray nozzle 18.

In the illustration of FIG. 3, an exemplary detection device 100 according to the invention is shown. Hereinafter, only the differences to the illustration in FIG. 1 are described.

The detection device 100 has a sensor unit 20, an evaluation unit 22 and a control unit 24. The sensor unit 20 includes a first sensor 26 and a second sensor 28 disposed at a distance A1 to the first sensor 28.

The first sensor 26 and the second sensor 28 are different from another with regard to their directivity. The first sensor has the first directivity and the second sensor has the second directivity, wherein the directivity is smaller in width than the second directivity.

If both sensors 26 and 28 are operated in alternation, the first sensor 26 transmits a first transmission signal S1 at a first point in time t1. The emitted transmission signal S1 is reflected on the various layers of a plant 30 located underneath, for example, the plant tip and/or one or more plant leaves, and/or the ground lying underneath. The reflections are received as a first reflection signal R1 by the first sensor 26 and transmitted to the evaluation unit 22.

Subsequently, at a second point in time t2=t1+Dt, the second sensor 28 sends out a second transmission signal 28 and detects the reflections as a second reflection signal R2, which is also transmitted to the evaluation unit 22.

By means of the evaluation unit 22 and based on the reflection signals R1 and R2, subsequently the distance A1 from the tip to the sensor unit 20, the distance A2 to the ground as well as the distance A3 to intermediate reflection layers, e.g., leaves, is ascertained.

In addition, based on the reflection signals R1 and R2, a horizontal distance D1 between neighboring plants is ascertained.

On the basis of the ascertained distances, the distance of the spray nozzles to the plants is set by means of the control unit 24. Furthermore, the ascertained distances make it possible to adjust the amount of fertilizer to be dispensed to the height of the plants and/or the plant density.

If the detection device is moved across an entire field and the distances A1, A2 and A3 as well as the horizontal distances D1 are detected at regular timed intervals, then it is also possible to ascertain both an average plant height and an average plant density for the entire field, whereby an expected yield can be estimated.

In the illustration of FIG. 4, an example for a reflection signal R1 over time t is plotted. Each reflection, i.e., each reflection plane, creates one peak in the reflection signal.

In the ideal case, a first peak is generated by the plant tip and a last peak by the ground and possibly further intermediate peaks by further reflection planes of the plant, for example, the leaves.

The peaks, i.e., the individual reflections, can also merge, or various reflections or even scattering may overlap.

The peaks are ascertained by means of thresholding queries or by means of one or more threshold filters. In order to more accurately detect the individual reflection planes, it is advantageous to perform a combined query of a slope threshold and a height threshold or to use appropriate filters, e.g., digital filters.

The illustration of FIG. 5 displays the sound beams 40, 42, 44 of an ultrasonic sensor with variable transmitting power for three different transmitting powers.

The sound beams 40, 42 and 44 and thus the directivities for the different transmission powers each have different widths B1, B2 or B3. This makes it possible to realize the two directivities, which differ according to the invention, with the first sensor and without a second sensor.

Figure 6:
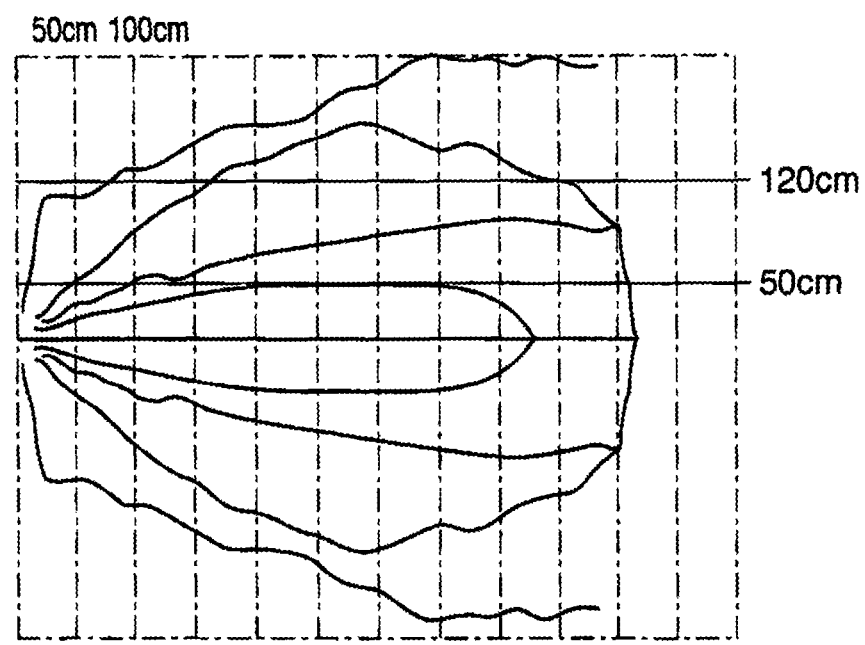

Alternatively, it is possible to use two different sensors, e.g., two different ultrasonic sensors, which differ at least in terms of directivity. In the illustration of FIG. 6, the sound beams of four different ultrasonic sensors are represented, which in particular all clearly differ in terms of their width.

The invention being thus described, it will be obvious that the same may be varied in many ways. Such variations are not to be regarded as a departure from the spirit and scope of the invention, and all such modifications as would be obvious to one skilled in the art are to be included within the scope of the following claims

What is claimed is:

1. An agricultural detection device comprising:
   a sensor unit comprising a first sensor with a first directivity, the first sensor being configured to emit a first transmission signal and to receive a first reflection signal;
   an evaluation unit; and
   a control unit,
   wherein the first sensor has a second directivity and emits a second sensor signal with the second directivity and receives a second reflection signal, or the sensor unit comprises a second sensor arranged adjacent to the first sensor with a second directivity for emitting the second transmission signal and for receiving the second reflection signal,
   wherein the first directivity is smaller in width than the second directivity,
   wherein the control unit switches between the first directivity and the second directivity,
   wherein the evaluation unit ascertains at least a structure of plants, a height value and a density of the plants from the first reflection signal and the second reflection signal,
   wherein the evaluation unit determines a horizontal distance between neighboring plants from the first reflection signal and the second reflection signal, and
   wherein the sensor unit is provided on a spray boom of a field sprayer of a vehicle, the sensor unit being arranged adjacent to at least one spray nozzle of the spray boom.

2. The agricultural detection device according to claim 1, wherein the first sensor is an ultrasonic sensor.

3. The agricultural detection device according to claim 1, wherein the first directivity is a sound beam and wherein the sound beam has a width between 30 cm and 70 cm at a distance of 1 m to the first sensor.

4. The agricultural detection device according to claim 1, wherein the second directivity is a sound beam and wherein the sound beam has a width between 80 cm and 120 cm at a distance of 1 m to the first sensor.

5. The agricultural detection device according to claim 1, wherein the first sensor is an ultrasonic sensor, wherein the second sensor is a radar sensor with a detection field as the second directivity, and wherein the detection field has a width between 80 cm and 2 m at a distance of 1 m to the radar sensor.

6. The agricultural detection device according to claim 1, wherein the first sensor is an ultrasonic transducer with a variable directivity.

7. A detection method for the detection of agricultural objects, the method comprising:
   providing a sensor unit having a first sensor, an evaluation unit, and a control unit, the first sensor being operatively connected with the evaluation unit and the control unit;
   emitting, via the first sensor with a first directivity, a first transmission signal at timed intervals and receiving subsequently, a first reflection signal; and
   transmitting, via the first sensor with a second directivity or a second sensor disposed adjacent to the first sensor with a second directivity, a second transmission signal at timed intervals and receiving a second reflection signal, wherein the first directivity is smaller in width than the second directivity, wherein a height value, a structure of plants and a density of the plants are ascertained by the evaluation unit via the first reflection signal and the second reflection signal, wherein the evaluation determines a horizontal distance between neighboring plants from the first reflection signal and the second reflection signal, and wherein the sensor unit is provided on a spray boom of a field sprayer of a vehicle, the sensor unit being arranged adjacent to at least one spray nozzle of the spray boom.

8. The detection method according to claim 7, wherein the second transmission signal is emitted via the second sensor, and wherein the first transmission signal and the second transmission signal are emitted simultaneously.

9. The detection method according to claim 7, wherein the first transmission signals and the second transmission signals are emitted in alternation.

10. The detection method according to claim 7, wherein the first transmission signals are generated by a first ultrasonic transducer.

11. The detection method according to claim 7, wherein the second transmission signals are generated by a second ultrasonic transducer or by a radar sensor.

12. The detection method according to claim 7, wherein, in the first and second reflection signals, a rising slope is ascertained via a slope threshold.

13. The detection method according to claim 12, wherein, in the first and second reflection signals, a height value is ascertained via a height threshold.

14. The detection method according to claim 13, wherein the height value is ascertained after exceeding the slope threshold and the height threshold.

* * * * *